United States Patent [19] [11] 4,123,844
Kurz [45] Nov. 7, 1978

[54] VIBRATIONAL MOUTH PAD ORTHODONTIC APPLIANCE

[76] Inventor: Craven H. Kurz, No. 1 North Star, Apt. 106, Marina del Rey, Calif. 90291

[21] Appl. No.: 752,404
[22] Filed: Dec. 20, 1976
[51] Int. Cl.² ............................................. A61C 7/00
[52] U.S. Cl. ..................................... 32/14 D; 32/14 A
[58] Field of Search ............... 32/14 R, 58, DIG. 4, 32/20, 14 D, 14 A; 128/62 A, 24 A, 409

[56] References Cited

U.S. PATENT DOCUMENTS

| 1,826,434 | 10/1931 | Reiss | 128/62 A |
| 2,880,509 | 4/1959 | Strickler | 32/14 D |
| 2,983,046 | 5/1961 | Jenkins | 32/14 D |
| 3,385,291 | 5/1968 | Martin | 128/62 A |
| 3,401,690 | 9/1968 | Martin | 128/62 A |
| 3,660,900 | 5/1972 | Andrews | 32/14 A |
| 4,011,616 | 3/1977 | Kennedy | 128/62 A |

Primary Examiner—Louis G. Mancene
Assistant Examiner—John J. Wilson
Attorney, Agent, or Firm—Keith D. Beecher

[57] ABSTRACT

An orthodontic appliance in the form of a vibrational pad is provided. The pad is held in place in the mouth of the patient by an external head gear. A vibrational electric motor is mounted on the head gear, and the motor is mechanically coupled to vibrational elements within the mouth pad. The mouth pad is used in conjunction with conventional orthodontic appliances, and it serves to vibrate the teeth being moved by the conventional orthodontic appliances so as to disseminate heavy orthodontic pressures of the conventional appliance to a larger boney mass resulting in lighter more physiological pressure in a larger area. This will increase the speed and efficiency of the orthodontic movement, minimize pain to the patient, and reduce root resorption and horizontal bone loss.

2 Claims, 4 Drawing Figures

VIBRATIONAL MOUTH PAD ORTHODONTIC APPLIANCE

BACKGROUND OF THE INVENTION

Teeth which are moved by conventional fixed orthodontic appliances have continual forces exerted on them by way of the arch wires, springs, elastic traction devices and/or head gear. This constant force is translated to the alveolar bone around the teeth. The pressure on the bone causes constriction of the blood vessels and acts to squeeze out the tissue fluid as the root of the tooth is approached.

Blood supply is necessary for orthodontic tooth movement. Histologically the osteoclasts are the cells responsible for bone resorption, and the osteoblasts are the cells responsible for rebuilding the bone. Pressure in the bone tissue causes the production of osteoclasts, and negative pressure or tension in the bone tissue causes the production of osteoblasts. In order for a tooth to move through the bone there must be osteolcastic cell activity to resorb the bone in the direction of tooth movement, and there must also be osteoblastic activity for new bone formation on the side of the tooth experiencing negative pressure or tension. The greater the blood supply to an area, the greater the osteoclastic and osteoblastic cellular activity.

In conventional fixed orthodontic therapy, the pressure applied to a tooth is translated to the immediately adjacent tissue and there is a reduction of blood supply to that area. This lack of blood supply causes necrosis of the bone on the pressure side. Blood vessels in adjacent areas which are far enough away from the tooth so that their blood flow is not cut off carry osteoclasts to the area to remove the necrostized bone, and this is called reverse resorption. The tooth then moves into the area where the necrotic bone was removed, and this causes the new area of high pressure, reduced blood flow and necrosis, which again must be removed by reverse resorption.

The aforesaid prior art method of orthodontic tooth movement is pathological and not physiological. The aforesaid method results in pain to the patient, relatively slow movement of the tooth, root resorption and irreversible horizontal bone loss. During orthodontic movement of the tooth by the aforesaid method, the tooth is not stable but is loosened to some degree, resulting in an unstable occlusion.

For optimal orthodontic movement the area in which the tooth is moving should have abundant blood supply. Blood carries the cellular elements for rapid, high concentration of osteoclasts. The greater the blood supply, the greater the cellular activity, and the faster the bone in the direct pressure area is resorbed and the faster the resorption by-products are removed. Also, increased blood supply increases the apposition of bone in the tension or negative pressure side of the tooth causing increased stability of the tooth during the movement.

To increase the blood supply to a pressure area and thereby reduce the ecsemia there must be a dissemination of pressure from the immediate bone in the root area to the adjacent bone and tissues. This will reduce the magnitude of pressure on the immediate bone, reduce vascular constriction due to pressure, and deliver to a larger tissue area pressure that are more optimal for high concentration of osteoclasts and osteoblasts.

Bone recontouring will then take place by a process of front face resorption in the bone immediately adjacent to the tooth being subjected to the orthodontic pressure. This is the most physiological method of bone resorption for tooth movements, and it also results in the fastest and most efficient movement of the tooth.

Under such conditions, there is no area of necrosis so that no pain sensation is evoked. When the direct pressure is light there is no root resorption or irreversible horizontal bone loss. The osteoclastic activity is accelerated as is the osteoblastic activity and consequently there is continual speedy apposition of new bone on the tension or negative pressure side of the tooth resulting in a more stable occlusion during tooth movement.

The pressure dissemination which results in the desirable results described in the preceding paragraph is achieved in accordance with the concepts of the present invention by providing a vibrating mouthpiece in the mouth of the patient which disseminates pressures that are being applied by conventional orthodontic appliances to a large bone mass, and this results in eliminating any area of reduced blood supply. Also, the forces that are now being applied to the roots of the teeth are no longer static, but are dynamic, which lead to a reduction of boney tissue resistance as the roots are now vibrated-through the boney tissue mass along paths of least resistance.

DETAILED DESCRIPTION OF THE ILLUSTRATED EMBODIMENT

Figure 1:
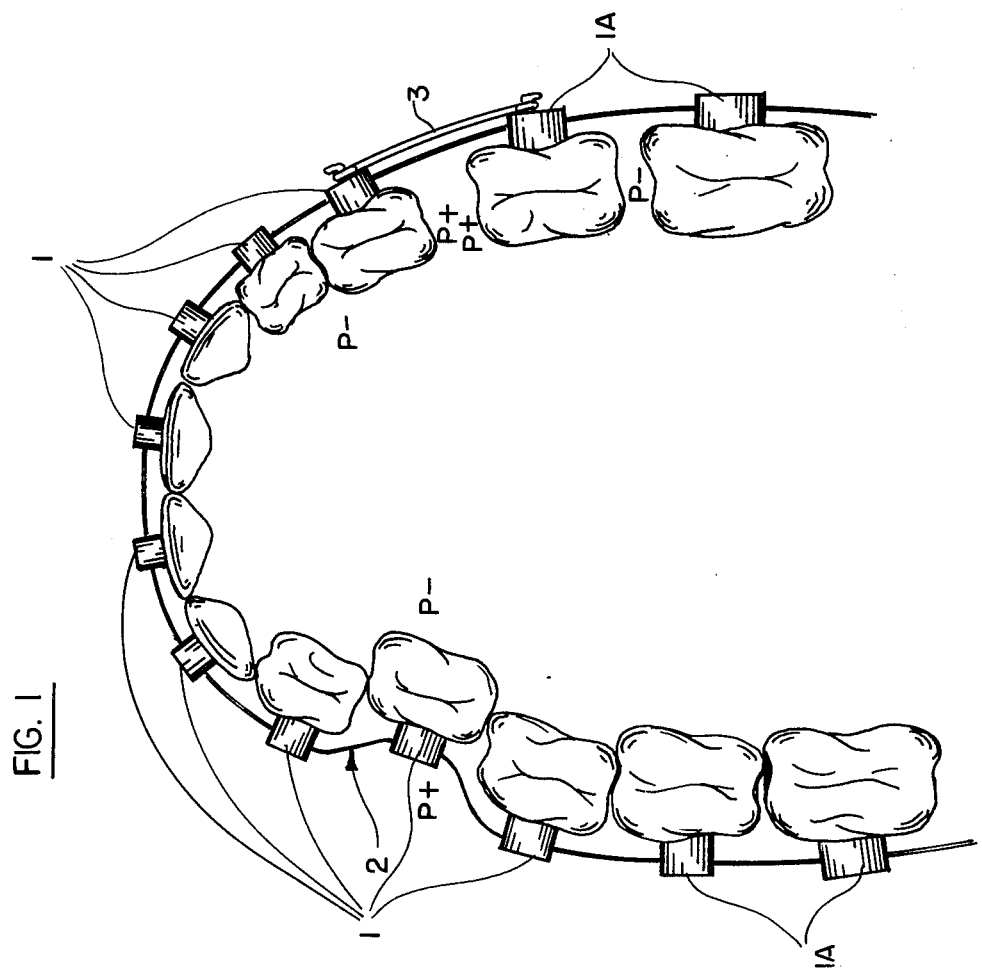
FIG. 1 is a somewhat schematic representation of a dental arch having a usual prior art conventional fixed orthodontic appliance mounted on the teeth thereof.

In the representation of FIG. 1, a plurality of brackets, such as the brackets 1, and a plurality of tubes such as the tubes 1A are affixed to the teeth, and the brackets and tubes are interconnected by an arch wire 2 which applies a force to the misalligned teeth. An elastic ligature 3 is also provided for pulling two adjacent teeth together. The pressure area in the adjacent bone tissue are designated P+ for positive pressure and P− for negative pressure or tenstion. The areas designated P+ are the areas of osteoclastic activity, and the areas designated P− are the areas of osteoblastic activity.

Figure 2:
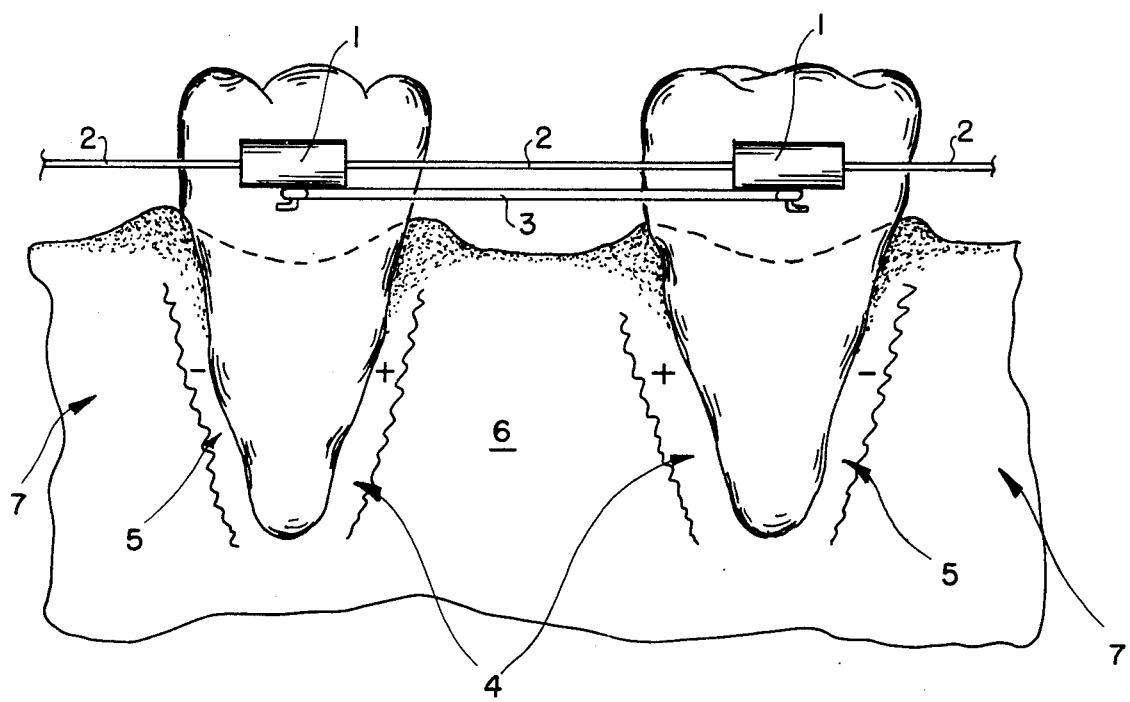
FIG. 2 is a schematic representation of a pair of adjacent teeth being subjected to an elastic force during prior art orthodontic treatment tending to pull the two teeth together.

The representation of FIG. 2 shows in more detail the two adjacent teeth which are pulled together by the elastic ligature 3, in accordance with conventional prior art orthodontic therapy. The areas designated 4, represents adjacent bone subjected to the pressure of the roots of the teeth. This area represents the immediately adjacent bone which is under high pressure during conventional prior art orthodontic treatment, and blood vessels in this area are compressed which results in a reduced flow of blood. The areas designated 5 represent the bone areas which are subjected to negative pressure or tension during the conventional prior art orthodontic treatment. The tension is high during the prior art treatment, and there is a tearing of tissue in these areas. The adjacent boney tissue with less pressure on its blood vessels is designated 6, and adjacent boney tissue with reduced tension is designated 7.

Figure 3:
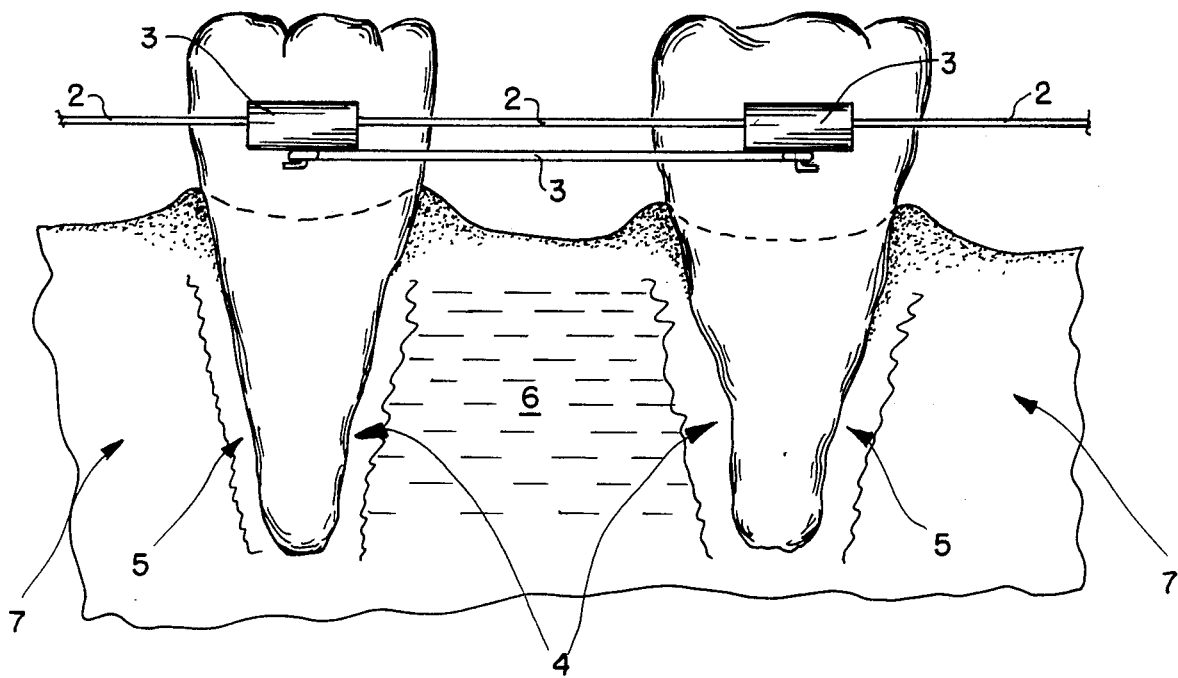
FIG. 3 is a view like FIG. 2, but showing the effect when the teeth are subjected to vibrational forces.

In the representation of FIG. 3, the adjacent teeth are vibrated by the appliance of the invention so that the pressure on the bone in the adjacent area of the root is disseminated from the areas 4 and 5 to the areas 6 and 7. The pressures on the bone in areas 4 and 5 are reduced because the pressures are vibrated and consumed by tissue in the areas 6 and 7. Thus the blood supply in areas 4 and 5 is accelerated rather than reduced.

Due to the ultra-sonic vibration by the appliance of the invention, the bone in the entire area 6 between the teeth is lightly pressurized, and throughout this area there is increased blood flow, increased cellular activity, increased bone resorption by physiological front-face process starting at the area 4. The vibrational breakdown of tissue resistance to pressure produces a path for the movement of the tooth with minimal resistance. The bone in area 7 has a high-tension negative force vibrated into it and, when absorbed by this larger area, the force is lighter, and there is an increase in blood flow which hastens the formation of new bone in area 5.

Figure 4:
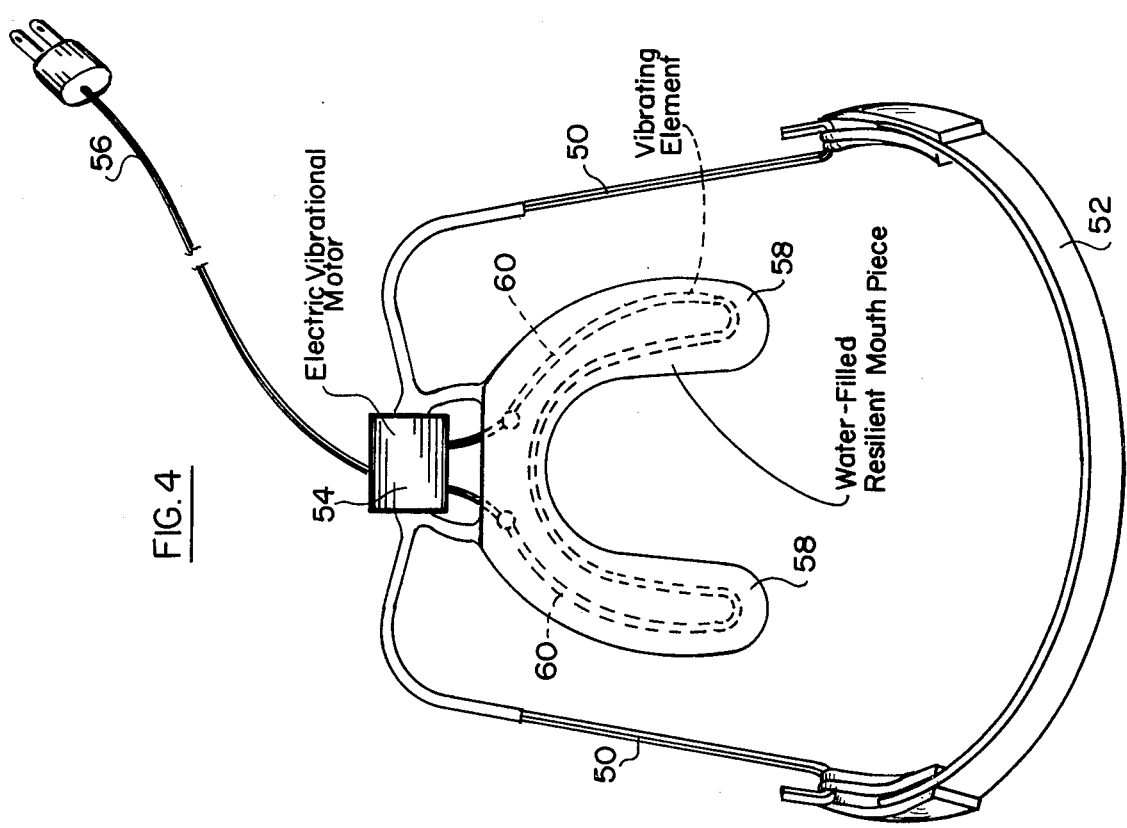
FIG. 4 is a top plan view of an orthodontic appliance constructed to incorporate the concepts of the present invention.

The orthodontic appliance of the invention which creates the vibrational forces is shown, in one of its embodiments in FIG. 4. The appliance includes the usual extra oral bow 50 which is supported around the head of the patient by an elastic neck strap 52. An electric vibrational motor 54 is mounted on the bow 50 adjacent to the patient's mouth. Motor 54 may be energized from the usual alternating current outlet through an electric cord 56, or it may contain a replaceable or rechargeable battery.

A mouth piece 58 in the form, for example, of a resilient container pad filled with water or other appropriate fluid, is mounted on the bow 50, and the container has a shape to extend into the mouth of the patient to be clenched between the patient's teeth. An appropriate metallic vibrating element 60 is mounted within the container 58, and the element is mechanically attached to the motor 54.

When the motor 54 is energized, the vibrating element 60 sets up ultra-sonic vibrations within the container 58, and these vibrations are transmitted to the teeth to disseminate the high pressures in the areas of the moving teeth to larger areas of bone, thereby to reduce the overall pressure on the immediately adjacent bone. This action, as explained above, results in continued high vascular supply to the affected areas which, in turn, increases cellular activity. The mouth piece 58 of FIG. 4 causes pressure on the teeth to be vibrated into the boney areas adjacent to the teeth resulting in a breakdown of tissue resistance. This serves to help the root of each tooth being moved to find its path of least resistance through the boney fibers.

Use of the appliance of FIG. 4 results in increasing the speed and efficiency of the orthodontic movement, minimizes pain to the patient, and reduces root resorption and horizontal bone loss.

As described above, the vibrating mouth piece 58 of the invention is held in place by the external head gear apparatus.

In a constructed embodiment of the invention, the mouth piece 58 is approximately 5 millimeters thick, and is available in various sizes so that it can be fitted to different patients to be used in conjunction with conventional orthodontic treatment and appliances.

During the operation of the mouth piece of the invention, vibration of element 60 inside the mouth piece transmits ultra-sonic vibrations into the fluid, and the fluid serves to transmit the ultra-sonic vibrations to all the teeth of the patient contacted by the mouth piece in both the upper and lower arches simultaneously. The appliance of the invention serves to reduce stresses on both arches at the same time. It also unlocks the occlusion so that cusps are not interlocked by the bite, which might otherwise prevent teeth from moving.

The appliance of the invention can be worn continually, or it may be placed in the patient's mouth by the orthodontist after the conventional fixed appliance has been adjusted, and left in the mouth for a specified period of time. This would be an attempt to disseminate immediate pressure caused by orthodontic adjustment while the patient is still in the treatment area.

Although an electric vibrational motor 54 is shown in FIG. 4 as coupled to an element 60 within the mouth piece to produce vibrations in fluid within the mouth piece; these elements may be replaced by an hydraulic pump mounted on the bow 50, and which operates to produce pulsations within the mouth piece, so that the water or other liquid therein may transmit the desired ultra-sonic pulsations to all of the teeth of the patient contacted by the mouth piece.

It will be appreciated that while particular embodiments of the invention have been shown and described, modifications may be made. It is intended in the claim to cover the modifications which come within the spirit and scope of the invention.

What is claimed is:

1. An orthodontic appliance comprising: a plurality of brackets affixed to the teeth of the patient and an arch wire connected to said brackets to cause the roots of the teeth to exert a predetermined static pressure on the adjacent bony tissue; a pad adapted to fit into the mouth of the patient to be clenched between the teeth of the patient; means comprising an electric vibrational motor and a vibrational element mechanically coupled to the motor and extending into said pad for creating vibrational movement in the pad for transmission to the teeth of the patient to vibrate the teeth so as to cause vibrational dynamic forces to be superimposed on the static forces on the roots of the teeth in a direction to cause a reduction in the resistance of the adjacent bony tissue to movement of the teeth through such tissue; and means for mounting the pad in the mouth of the patient comprising an extra oral head gear including a bow, said motor being mounted on said bow.

2. The orthodontic appliance defined in claim 1, in which said pad comprises a flexible container containing a selected fluid.

* * * * *